US007855195B2

(12) United States Patent
Buntinx

(10) Patent No.: US 7,855,195 B2
(45) Date of Patent: *Dec. 21, 2010

(54) METHOD OF TREATING MENTAL DISORDERS USING D4 AND 5-HT2A ANTAGONISTS, INVERSE AGONISTS OR PARTIAL AGONISTS

(75) Inventor: Erik Buntinx, Alken (BE)

(73) Assignee: PharmaNeuroBoost N.V., Alken (BE)

( * ) Notice: Subject to any disclaimer, the term of this patent is extended or adjusted under 35 U.S.C. 154(b) by 1341 days.

This patent is subject to a terminal disclaimer.

(21) Appl. No.: 10/752,423

(22) Filed: Jan. 6, 2004

(65) Prior Publication Data

US 2005/0119248 A1 Jun. 2, 2005

Related U.S. Application Data

(63) Continuation-in-part of application No. 10/725,965, filed on Dec. 2, 2003.

(51) Int. Cl.

| | |
|---|---|
| ***A01N 43/46*** | (2006.01) |
| ***A01N 43/26*** | (2006.01) |
| ***A01N 33/02*** | (2006.01) |
| ***A01N 33/24*** | (2006.01) |
| ***A61K 31/535*** | (2006.01) |
| ***A61K 31/445*** | (2006.01) |
| ***A61K 31/335*** | (2006.01) |

(52) U.S. Cl. .................... 514/217; 514/232.8; 514/317; 514/649; 549/467

(58) Field of Classification Search ................. 514/567, 514/232.8, 217, 317, 649; 549/467
See application file for complete search history.

(56) References Cited

U.S. PATENT DOCUMENTS

| | | | | |
|---|---|---|---|---|
| 4,797,419 | A | 1/1989 | Moos et al. | |
| 5,364,857 | A | 11/1994 | Bode Greuel | |
| 5,446,070 | A | 8/1995 | Mantelle | |
| 5,554,383 | A | 9/1996 | Dodman | |
| 5,635,213 | A | 6/1997 | Nystrom et al. | |
| 5,759,837 | A | 6/1998 | Kuhajda et al. | |
| 5,762,960 | A | 6/1998 | Dodman | |
| 5,780,474 | A | 7/1998 | Brocco et al. | |
| 6,150,353 | A * | 11/2000 | Broekkamp et al. | 514/214.02 |
| 6,191,133 | B1 | 2/2001 | Coppen | |
| 6,300,354 | B1 | 10/2001 | Steiner et al. | |
| 6,358,698 | B1 | 3/2002 | Weiner et al. | |
| 2002/0086899 | A1 * | 7/2002 | Sanchez et al. | 514/469 |
| 2003/0032636 | A1 * | 2/2003 | Cremers et al. | 514/220 |
| 2004/0002482 | A1 | 1/2004 | Dudley et al. | |
| 2004/0213816 | A1 | 10/2004 | Weiner et al. | |
| 2005/0119249 | A1 | 6/2005 | Buntinx | |
| 2005/0119253 | A1 | 6/2005 | Buntinx | |
| 2005/0148018 | A1 | 7/2005 | Weiner et al. | |
| 2005/0203130 | A1 | 9/2005 | Buntinx | |
| 2005/0261278 | A1 | 11/2005 | Weiner et al. | |
| 2005/0261340 | A1 | 11/2005 | Weiner et al. | |
| 2005/0288328 | A1 | 12/2005 | Weiner et al. | |
| 2006/0199842 | A1 | 9/2006 | Weiner et al. | |
| 2006/0264465 | A1 | 11/2006 | Weiner et al. | |
| 2006/0264466 | A1 | 11/2006 | Weiner et al. | |
| 2007/0078162 | A1 | 4/2007 | Buntinx | |

FOREIGN PATENT DOCUMENTS

| | | | |
|---|---|---|---|
| CA | 2461248 | | 9/2009 |
| DE | 40 39 631 | A | 6/1992 |
| DE | 4039631 | A1 | 6/1992 |
| EP | 1 541 197 | B1 | 3/2009 |
| WO | WO 98/11897 | A | 3/1998 |
| WO | WO 98/43646 | A | 10/1998 |
| WO | WO 00/64441 | A | 11/2000 |
| WO | 0141701 | A2 | 6/2001 |
| WO | WO 01/41701 | A2 | 6/2001 |
| WO | WO 01/98298 | A | 12/2001 |
| WO | WO 02/051833 | A | 7/2002 |

OTHER PUBLICATIONS

Prinssen et al. (E J of Pharmacology, 388, 2000, 57-67).*

Meyer et al. J of Pharmacokinetics and Biopharmaceutics, 24, 5, 1996.*

Hubble J P et al., entitled "Pre-clinical studies of pramipexole: clinical relevance," European Journal of Neurology Supplement, 2000, vol. 7 (Suppl. 1), pp. 15-20.

Silver D E et al., entitled "Initiating therapy for Parkinson's disease," Neurology, 1998, vol. 50 (Suppl. 6), pp. S18-S22.

www.biam2.org/www/Sub2783.html, entitled "Pipamperone Dichlorhydrate," Nov. 12, 2000, 1-4.

www.adiph.org/pic/pedia-neuroleptiques.pdf, entitled "Medicaments Psychotropes: Posologies Chez L'Enfant et L'Adolescent," Aug. 2001, 1-3.

Heiser P et al., entitled "The selective serotonin reuptake inhibitors and the newer antidepressants in child and adolescent psychiatry," Zeitschrift fur Kinder—und Jugendpsychiatrie und Psychotherpie Switzerland 30: 2002, 173-183.

(Continued)

*Primary Examiner*—Sreeni Padmanabhan
*Assistant Examiner*—Umamaheswari Ramachandran
(74) *Attorney, Agent, or Firm*—Amster, Rothstein & Ebenstein LLP

(57) ABSTRACT

The present invention relates to methods of treating of the underlying dysregulation of the emotional functionality of mental disorders (i.e. affect instability-hypersensitivity-hyperaesthesia-dissociative phenomena- . . . ) using compounds and compositions of compounds having D4 and/or 5-HT2A antagonistic, partial agonistic or inverse agonistic activity for. The invention also relates to methods comprising administering to a patient diagnosed as having a neuropsychiatric disorder a pharmaceutical composition containing (i) compounds having D4 antagonistic, partial agonistic or inverse agonistic activity and/or (ii) compounds having 5-HT2A antagonistic, partial agonistic or inverse agonistic, and/or (iii) any known medicinal compound and compositions of said compounds. The combined D4 and 5-HT2A antagonistic, partial agonistic or inverse agonistic effects may reside within the same chemical or biological compound or in two different chemical and/or biological compounds.

17 Claims, No Drawings

OTHER PUBLICATIONS

Carlier PR et al., Synthesis of a Potent Wide-Spectrum Serotonin-, Norepinephrine-, Dopamine- reuptake inhibitor (SNDRI) and a species-selective dopamine reuptake inhibitor based on the gamma-amino alcohol functional group, Bioorgan. Medicin. Chem. Let. 8, 1998, 487-492.

Fitzgerald K D et al., entitled "Risperidone Augmentation of Serotonin Reuptake Inhibitor Treatment of Pediatric Obsessive Compulsive Disorder," Journal of Child and Adolescent Psychopharmacology, vol. 9, No. 2, 1999, 115-123.

McDougle C J et al., entitled "A Double-blind. Placebo-Dontrolled Study of Risperidone Addition in Serotonin Reuptake Inhibitor-Refractory Obsessive-complusive Disorder," Arch Gen Psychiatry, vol. 57, Aug. 2000, 794-801.

Maina G et al., entitled "Antipsychotic agumentation for treatment resistant obsessive-compulsive disorder: what if antipsychotic is discontinued," Int. Clin. Psychopharm, 18, 2003, 23-28.

Hirose S et al., entitled "An Open Pilot Study Combining Risperidone and a Selective Serotonin Reuptake Inhibitor as Initial Antidepresant Therapy," J. Clin. Psych. 63, 2002, 733-736.

Truffinet P et al., Placebo-controlled study of the D4/5-HT2A antagonist fananserin in the treatment of schizophrenia. Am J. Psychiatry 156: 419-425, 1999.

Schindler T et al., entitled "Palliative medical management in anxiety and depression," Zeitschrift Fur Allgemeinmedizin, vol. 74, No. 21, Nov. 5, 1998, pp. 973-978.

Volmat R et al., entitled "The treatment of depressions by Cledial. Evolution and clinical state and handwriting," Psychologie Medicale, vol. 18, No. 10, 1986, pp. 1615-1622.

Fouks et al., entitled "Treatment of character disorders with a new butyrophenone: R. 3345 or pipamperone," Annales Medico-Psychologiques, vol. 124, No. 5, 1966, pp. 677-681.

Squelart P et al., entitled "Pipamperone (Dipiperon), a useful sedative neuroleptic drug in troublesome chronic psychotic patients," Acta Psychiatrica Belgica, vol. 77, No. 2, Mar. 1977, pp. 284-293.

Koch H J et al., entitled "Successful therapy of tardive dyskinesia in a 71-year-old woman with a combination of tetrabenazine, olanzapinr and tiapride," International Journal of Clinical Practice, vol. 57, No. 2, Mar. 2003, pp. 147-149.

Diebold K et al., entitled "Are psychoactive-drug-induced changes in plasma lipid and lipoprotein levels of significance for clinical remission in psychiatric disorders?" Pharmacopsychiatry, 1998, 31/2, pp. 60-67.

Grozinger M et al., entitled "Melperone is an inhibitor of the CYP2D6 catalyzed 0-demethylation of venlafaxine," Pharmacopsychiatry, vol. 36, No. 1, Jan. 3003, pp. 3-6.

Perugi G et al., entitled "Effectiveness of Adjunctive Gabapentin in Resistant Bipolar Disorder: Is it due to anxious-alcohol abuse comorbidity?" Journal of clinical Psychopharmacology, vol. 22, No. 6, 2002, pp. 584-591.

Wieling W et al., entitled "Initial orthostatic hypotension as a cause of recurrent syncope: A case report," Clinical Autonomic Research, vol. 11, No. 4, 2001, pp. 269-270.

Database Pharmaprojects 'Online! PJB Publications Ltd., Dec. 1999. Caesar accession No. 1498.

Adler L et al., entitled "Praxis Der Stationaeren Akutbehandlung Von Manien Retrospektive Vergleichsuntersuchung An Je 100 Patienten Zweier Psychiatrischer Sentren Practice of In-Patient Acute Treatment of Manias," Fortschritte Der Neurologie.

Psychiatrie, Stuttgart, vol. 62, No. 12, 1994, pp. 479-488.

Ansoms C et al., entitled "Sleep disorders in patients with severe mental depression: double-blind placebo-controlled evaluation of the value of pipamerone (Dipiperon)," Acta Psychiatrica Scandinavica, vol. 55, No. 2, Feb. 1977, pp. 116-122.

Leysen J E et al., entitled "Receptor interactions of new antipsychotics: Relation to Pharmacodynamic and Clinical Effects," International Journal of Psychiatry in Clinical Practice, vol. 2, No. 1, 1998, pp. S03-S17.

Vanhoenacker P et al., entitled "Efficient Expression of the Human Dopamine D4.2 Receptor: Positive Influence of Pipamperone on Expression Levels," Abstracts of the Society for Neuroscience, vol. 26, No. 1/2, 2000.

Schotte A et al., entitled "Risperidone compared with new and reference antipsychotic drugs: In vitro and in vivo receptor binding," Psychopharmacology, vol. 124, No. 1-2, 1996, pp. 57-73.

Woggon B, entitled "Pharmakologische depressionbehandlung pharmacological treatment of depression," Therapeutische Umschau, vol. 57, No. 2, 2000, pp. 81-89.

Van De Vijver Damc et al., entitled "Antipsychotics and Parkinson's disease: Association with disease and drug choice during the first 5 years of antiparkinsonian durg treatment," Eur J Clin Pharmacology, vol. 58, 2002, pp. 157-161.

Jovic Ni et al., entitled "Phenomenology and treatment of delirium in Alzheimer's disease!" Revue Medicale De La Suisse Romande, vol. 117, No. 9, Sep. 1997, pp. 655-658.

Engelborghs S et al., entitled "Amino acids and biogenic amines in cerebrospinal fluid of patients with Parkinson's disease," Neurochemical Research, vol. 28, No. 8, Aug. 2003, pp. 1145-1150.

Newman-Tancredit A et al., [35S]-guanosine-5'-0-(3-thio) triphosphate binding as a measure of efficacy at human recombinant dopamine D-4.4 receptors: Actions of antiparkinsonian and antipsychotic agents. Journal of Pharmacology and Experimental Therapeutics, vol. 282, No. 1, 1997 pp. 181-191

Tarazi F I et al., entitled "Role of dopamine D4 receptors in neuropsychiatric disorders," Journal of Neurochemistry, vol. 81, No. Supplement 1, Jun. 2002, p. 33. Abstract.

Tarazi F I et al., entitled "Dopamine D4 Receptors: Significance for Molecular Psychiatry at the Millennium," Molecular Psychiatry, vol. 4, No. 6, Nov. 1999, pp. 529-538.

Leopold N A, entitled "Risperidone treatment of drug-related psychosis in patients with parkinsonism," Movement Disorders. vol. 15, No. 2, Mar. 2000, pp. 301-304.

Hadj Tahar A et al., entitled "Antidyskinetic effect of JL-18, a clozapine analog, in parkinsonian monkeys," European Journal of Pharmacology, vol. 399, No. 2-3, Jul. 7, 2000, pp. 183-186.

Zesiewicz TA et al., entitled "Clozapine withdrawal symptoms in a Parkinson's disease patient," Movement Disorders: vol. 17, No. 6, Nov. 2002, pp. 1365-1367.

Faltraco F et al., Akuelle Therapiemoglichkeiten der Alzheimer Demenz (Current Therapeutical Strategies in Dementia), Neurol Rehabil 2003; 9 (1), pp. 15-22.

Etchepareborda M C, entitled "Neurocognitive and pharmacological approach to specific learning disorders," Database Medline Online!, US National Library of Medicine, Feb. 1999, and Revista De Neurologia, vol. 28, Suppl. 2, Feb. 1999, pp. S81-S93, Abstract.

Stahl S M et al., entitled "Examination of nightime sleep-related problems during double-blind, placebo-controlled trials of galantamine in patients with Alzheimer's disease," Current Medical Research and Opinion 2004, vol. 20, No. 4, 2004, pp. 517-524.

Meneses A et al., entitled "Are 5-HT (1B/1D) and 5-HT (2A/2B/2C) receptors involved in learning and memory processes?" IDrugs 1999, vol. 2, No. 8, 1999, pp. 796-801.

Wirz-Justice A et al., entitled "Haloperidol disrupts, clozapine reinstates the circadian rest-activity cycle in a patient with early-onset Alzheimer disease," Alzheimer Disease and Associated Disorders, vol. 14, No. 4, 2000, pp. 212-215.

Fahs H et al., entitled "Thymoregulateurs Dans L'Agitation et les Troubles Du Comportement Chez le Sujet Dement a Propos de Huit Cas, Anticonvulsivants and Aggresive Behaviors in Alzheimer's Disease. Eight Cases Reports," L'Encephale vol. 25, No. 2, 1999, pp. 169-174.

Werth E et al., entitled "Decline in long-term circadian rest-activity cycle organization in a patient with dementia," Journal of Geriatric Psychiatry and Neurology, vol. 15, No. 1, Apr. 2002, pp. 55-59.

Meltzer HY et al., entitled "Plasma clozapine levels and the treatment of L-Dopa-induced psychosis in Parkinson's disease. A high potency effect of clozapine," Neuropsychopharmacology, vol. 12, No. 1, 1995, pp. 39-45.

Munchau A et al., entitled "Pharmacological Treatment of Parkinson's Disease," Postgraduate Medical Journal, vol. 76, Oct. 2000, pp. 602-610.

USPTO Office Action dated Jan. 23, 2008 in connection with related U.S. Appl. No. 10/725,965, filed Dec. 2, 2003.

USPTO Office Action dated May 3, 2007 in connection with related U.S. Appl. No. 10/803,793, filed Mar. 18, 2004.

USPTO Office Action dated Aug. 10, 2007 in connection with related U.S. Appl. No. 10/984,683, filed Nov. 9, 2004.
USPTO Office Action dated Oct. 19, 2007 in connection with related U.S. Appl. No. 10/803,793, filed Mar. 18, 2004.
Müller T, entitled "Drug treatment of non-motor symptoms in Parkinson's disease," Expert Opinion on Pharmacotherapy, 2002, vol. 3, No. 4, pp. 381-388.
PERMAX prescription information, Eli Lilly Company, (http://www.fda.gov/medwatch/safety/2003/permax_Pl.pdf), revised Oct. 2, 2003, pp. 1-2.
USPTO Office Action dated Sep. 15, 2008 in connection with related U.S. Appl. No. 10/725,965, filed Dec. 2, 2003.
USPTO Office Action dated Sep. 2, 2008 in connection with related U.S. Appl. No. 10/803,793, filed Mar. 18, 2004.
USPTO Office Action dated Feb. 22, 2008 in connection with related U.S. Appl. No. 10/984,683, filed Nov. 9, 2004.
USPTO Office Action dated Oct. 21, 2008 in connection with related U.S. Appl. No. 10/984,683, filed Nov. 9, 2004.
Marek G J et al., "Synergistic Action of 5-HT2A Antagonists and Selective Serotonin Reuptake Inhibitors in Neuropsychiatric Disorders," Online publication: Sep. 13, 2002 at http://www.acnp.org/citations/Npp091302378, Neuropsychopharmacology 28: 402-12, 2003.
"Atypical Antipsychotic Agents: Medicaid Drug Use Review Criteria for Outpatient Use," cited in Sep. 15, 2008 Office Action in U.S. Appl. No. 10/725,965, pp. 1-14.
Communication From European Patent Office dated Oct. 13, 2008 in connection with European Patent Application No. 04 025 035.9-2112, 92 pages.
Stein D J et al, entitled "Risperidone augmentation of serotonin reuptake inhibitors in obsessive-compulsive and related disorders," J Clin Psychiatry, 1997, 58(3):119-122.
Albert U et al., entitled "Management of treatment resistant obsessive-compulsive disorder. Algorithms for Pharmacotherapy," Panminerva Med, 2002, 44(2):83-91.
Mohr N et al., entitled "Quetiapine augmentation of serotonin reuptake inhibitors in obsessive-compulsive disorders," Int J Psychopharmacol, 2002, 17(1):37-40.
Silver H, entitled "Selective serotonin reuptake inhibitor augmentation in the treatment of negative symptoms of schizophrenia," 2003, Int Clin Psychopharmacol, 18(6):305-313.
USPTO Office Action dated Jun. 10, 2009 in connection with U.S. Appl. No. 10/725,965, filed Dec. 2, 2003.
USPTO Office Action dated Jun. 2, 2009 in connection with U.S. Appl. No. 10/580,962, filed May 31, 2006.
Van Oekelen D et al., "Different regulation of rat 5-HT2A and rat 5-HT2C receptors in NIH 3T3 cells upon exposure to 5-HT and pipamperone," European Journal of Pharmacology 425 (2001) 21-32.
Meyer U A, "Overiew of Enzymes of Drug Metabolism," Journal of Pharmacokinetics and Biopharmaceutics, vol. 24, No. 5, 1996, 449-459.
Moore N et al., "Prospective, multicentre, randomized, double-blind study of the efficacy of escitalopram versus citalopram in outpatient treatment of major depressive disorder," Int Clin Psychopharmacol 20:131-137, 2005.
Montgomery S A et al., "Escitalopram versus venlafaxine XR in the treatment of depression," International Clinical Psychopharmacology 2006, 21:297-309.
Khan A et al., "Symptom Reduction and Suicide Risk in Patients Treated with Placebo in Antidepressant Clinical Trials," Arch Gen Psychiatry, vol. 57, Apr. 2000, 311-317.
USPTO Office Action dated Feb. 20, 2009 in connection with U.S. Appl. No. 10/803,793, filed Mar. 18, 2004.
Citalopram 10mg, 20mg and 40 mg Tablets, 2 pages, Actavis, Barnstaple UK, Date of last revsion Mar. 2007.
USPTO Office Action dated Jun. 10, 2009 in connection with related U.S. Appl. No. 10/725,965, filed Dec. 2, 2003.
USPTO Office Action dated Nov. 10, 2009 in connection with related U.S. Appl. No. 10/803,793, filed Mar. 18, 2004.
USPTO Office Action dated Jul. 21, 2009 in connection with related U.S. Appl. No. 10/984,683, filed Nov. 9, 2004.
USPTO Office Action dated Jun. 2, 2009 in connection with related U.S. Appl. No. 10/580,962, filed May 31, 2006.
Nelson, Craig J., et al., "Atypical Antipsychotic Augmentation in Major Depressive Disorder: A Meta-Analysis of Placebo-Controlled Randomized Trials." Am J Psychiatry, Sep. 2009, 166:980-991.
Peremans, Kathelijne et al., "Evaluation of serotonin-2A receptor occupancy with 123 I-5-I-R91150 and single-photon emission tomography before and after low-dose pipamperone administration in the canine brain." Nuclear Medicine Communications, 29:724-729, 2008.
Download from www.whocc.no/atcddd/welcome.html dated Aug. 20, 2009, 2 pages.
Buntinx, E. et al., Preclinical and clinical evidence for the efficacy of pipamperone in augmenting the antidepressant effects of the SSRI citalopram. International Journal of Neuropsychopharmaccology, vol. 1, supplement 1, p. 190, Jul. 2008.
Buntinx E et al., Preclinical and Clinical Evidence for the Efficacy of Pipamperone in Augmenting the Antidepressant Effects of the SSRI Citalopram. Poster presented at the XXVI Collegium Internationale Neuro-Psychopharmacologicum (CINP) Congress Jul. 13-17, 2008, Munich, Germany and Summary Expected Receptor Occupancy (RO) of Pipamperone in vivo.
Download, "Panic Attacks Anxiety Attacks Self-Help Anxieties OCD Social Anxiety Disorder." http://www.anxieties.com/med-intro.php, Dec. 3, 2009, pp. 1-5.
USPTO Office Action dated Apr. 14, 2010 in connection with U.S. Appl. No. 10/580,962, filed May 31, 2006.
Caley C F, entitled "Extrapyramidal Reactions from Concurrent SSRI and Atypical Antipsychotic Use," Can J Psychiatry (1998), vol. 43(3), pp. 307-308.
Brown E S, entitled "Extrapyramidal Side Effects with Low-Dose Risperidone," Can J Psychiatry (1997), vol. 42(3), pp. 325-326.
USPTO Notice of Allowance and Fee(s) Due dated Aug. 10, 2010 in connection with U.S. Appl. No. 10/725965, filed Dec. 2, 2003.
USPTO Office Action dated Jun. 8, 2010 in connection with U.S. Appl. No. 10/803,793, filed Mar. 18, 2004.
USPTO Office Action dated Jun. 23, 2010 in connection with U.S. Appl. No. 10/984,683, filed Nov. 9, 2004.
Buntinx E et al., Low dose pipamperone, enhancing antidepressant effect of citalopram, occupies 5HT2A 50-60% leaving D2 nearly drug free, The Journal of the European College of Neuropsychopharmacology, vol. 20, Supp. 3, Aug. 2010, S3968397, along with poster.
Dierick, Michel et al., "A Double-Blind Comparison of Venlafaxine and Fluoxetine for Treatment of Major Depression in Outpatients," Prog. Neuro-Psychopharmacol. & Biol. Psychiat., 1996, vol. 20. pp. 57-71.
Remington's Pharmaceutical Sciences, "Structure Activity Relationship and Drug Design," 1980, pp. 420-425.
Stella, Valentino J. et al., "Prodrug strategies to overcome poor water solubility," Advanced Drug Delivery Reviews 59 (2007) 677-694.
Hegerl, Ulrich et al., "The seratonin syndrome scale: first results on validity," Eur Arch Psychiatry Clin Neurosci (1998) 248: 96-103.

* cited by examiner

METHOD OF TREATING MENTAL DISORDERS USING D4 AND 5-HT2A ANTAGONISTS, INVERSE AGONISTS OR PARTIAL AGONISTS

CROSS REFERENCE TO RELATED APPLICATION

This application claims the benefit of and is a continuation-in-part of U.S. application Ser. No. 10/725,965, filed Dec. 2, 2003, entitled "Method of Treating Mental Disorders Using D4 and 5-HT2A Antagonists, Inverse Agonists or Partial Agonists," and naming Erik Buntinx as the inventor.

FIELD OF THE INVENTION

The invention relates to the field of neuropsychiatry. More specifically, the invention relates to methods of treating the underlying dysregulation of the emotional functionality of mental disorders using of compounds having D4 and/or 5-HT2A antagonist, inverse agonist or partial agonist activity.

BACKGROUND OF THE INVENTION

Clinical or real effectiveness of psychopharma is very rare via common pooping-out, many treatment-refractory patients and up to half of patients fail to attain remission (S. M. Stahl, Essential Psychopharmacology, 2000). Implications of not attaining remission for Mental Disorders are increased relapse rates, continuing functional impairment and increased suicide rate.

Clinical causes of not attaining remission by the Current Psychopharmacological Compounds are inadequate early treatment, underlying dysregulation of the emotional functionality (affect instability-hypersensitivity-hyperaesthesia-dissociative phenomena . . . ) and competitive antagonism.

Dysregulation of the HPA axis has frequently reported in patients with psychiatric disorders, and is among the most robustly demonstrated neurobiological changes among psychiatric patients (D. A. Gutman and C. B. Nemeroff, Biological Psychiatry, 2002). The resulting elevated plasma cortisol concentrations leads to an enhanced binding of serotonin for the 5-HT2A receptor (E. A. Young, Arch Gen Psychiatry/Vol 60, January 2003).

Results suggest that cortical D2 dopamine receptors are a common target of traditional and atypical antipsychotics for therapeutic action. Higher in vivo binding to the D2 receptors in the cortex than in the basal ganglia is suggested as an indicator of favourable profile for a putative antipsychotic compound (X. Xiberas and J. L. Martinot; The British Journal of Psychiatry (2001) 179: 503-508).

Data demonstrate that dopamine D4 receptors play an important role in the induction of behavioral sensitization to amphetamine and accompanying adaptations in pre- and postsynaptic neural systems associated with the mesolimbocortical dopamine projections (D. L. Feldpausch et al; The journal of pharmacology and experimental therapeutics Vol. 286, Issue 1, 497-508, July 1998). Further, results show that dopamine D4 receptor antagonism in the brain does not result in the same neurochemical consequences (increased dopamine metabolism or hyperprolactinemia) observed with typical neuroleptics (Smita Patel et al; The journal of pharmacology and experimental therapeutics Vol. 283, Issue 2, 636-647, 1997).

However, the selective D4 dopamine receptor antagonist L-745,870 was ineffective as an antipsychotic for the treatment of neuroleptic responsive inpatients with acute schizophrenia (Kramer M S et al; Arch Gen Psychiatry 1997 December; 54(12):1080.)

There is thus a growing need for a more efficient therapy and more efficient, selective and efficacious medicaments for treating mental disorders.

SUMMARY OF THE INVENTION

The present invention relates to the use of compounds and pharmaceutical compositions having D4 and/or 5-HT2A antagonistic, partial agonistic or inverse agonistic activity for the treatment of the underlying dysregulation of the emotional functionality of mental disorders (i.e. affect instability-hypersensitivity-hyperaesthesia-dissociative phenomena- . . . ) and to methods entailing administering to a patient diagnosed as having a neuropsychiatric disorder a pharmaceutical composition containing (i) compounds having D4 antagonistic, partial agonistic or inverse agonistic activity and/or (ii) compounds having 5-HT2A antagonistic, partial agonistic or inverse agonistic, and/or (iii) any known medicinal compound and compositions of compounds. The combined D4 and 5-HT2A antagonistic, partial agonistic or inverse agonistic effects may reside within the same chemical or biological compound or in two different chemical or two different biological compounds or in a combination of a chemical & biological compound.

In a more preferred embodiment of the invention, said composition is administered to a patient in a dose ranging between 0.5 μg and 300 mg for each of the active ingredients.

According to a first embodiment the invention relates to a method for treating a disease or disorder with an underlying dysregulation of the emotional functionality comprising the use of a compound having (i) a selective affinity for the Dopamine-4 (D4) receptor with a pKi value equal to or higher than 8 towards the D4 receptor and less than 8 towards other Dopamine receptors, and (ii) a selective affinity for the 5-HT2A receptor with a pKi value equal to or higher than 8 towards the 5-HT2A receptor and less than 8 towards other 5HT receptors and wherein said compound is administered to a patient in a dose ranging between 5 and 15 mg of the active ingredient, preferably said compound is PIPAMPERONE.

In a preferred embodiment, the disease or disorder to be treated with PIPAMPERONE is selected from the group comprising anxiety disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

The invention also relates to a method of treating a disease or disorder with an underlying dysregulation of the emotional functionality wherein a second compound is administered simultaneously with, separate from or sequential to the first compound as defined above to augment the therapeutic effect of said second compound on said disease, or to provide a faster onset of the therapeutic effect of said second compound on said disease. Preferably, the disease or disorder to be treated is selected from the group comprising mood disorders, anxiety disorders, schizophrenia and other psychotic disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

In a preferred embodiment, the invention relates to any of the methods described herein wherein the first compound is administered daily at least one day before administering said second compound. Preferably said second compound is a selective serotonine re-uptake inhibitor, for instance chosen from the group comprising, but not limited to, CITALOPRAM, fluoxetine, venlafaxine, fluvoxamine, paroxetine, sertraline, milnacipran and duloxetine or a pro-drug or an active metabolite thereof, or a pharmaceutically acceptable salt thereof. More preferably, said serotonin re-uptake inhibitor is CITALOPRAM and is administered in a dose ranging between 10 and 40 mg of the active ingredient.

According to another preferred embodiment, said second compound is a nor-epinephrine re-uptake inhibitor, preferably chosen from the group comprising, but not limited to, tandamine, pirandamine, ciclazindol, fluparoxan, lortalamine, talsupram, talopram, prindamine, nomifensine, viloxazine, tomoxetine, duloxetine, venlafaxine, milnacipran and reboxetine, or a pro-drug or an active metabolite thereof, or a pharmaceutically acceptable salt thereof.

According to another preferred embodiment, said second compound is a neuroleptic agent, preferably chosen from the group comprising, but not limited to, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, DU-127090, ORG-5222, SM-13496, amisulpride, CP-361428, Lu 35-138, balaperidone, S-18327, WAY-135452, eplivanserin, E-5842, SR-31742, NE-100, osanetant, SR-141716, SR-48692, BSF-201640, BSF-190555, LAX-101a, sarizotan, CX-691 and SB-271046, or a pro-drug or active metabolite thereof, or a pharmaceutically acceptable salt thereof.

According to another preferred embodiment, said second compound is a neurokinin-1 (NK1) antagonist, preferably chosen from the group comprising but not limited to MK-0869, GW597599, GW679769, GW823296, Compound A, NKP608, CP-96345 (cis-3-(2-methoxybenzyl-amino-2-benzhydrylquinuclidine), CP-122721, CP-99994, GR-82334 (D-Pro9-[Spiro-y-lactam]-Leu10,Trp11)-Physalaemin(1-11)), R673, TAK-637, RPR100893 (perhydroisoindolol), RP-67580, LY303870, SR-140333 and trans-4-hydroxy-1-(1H-indol-3-ylcarbonyl)-L-prolyl-N-methyl-N-(phenylmethyl)-L-tyrosineamide (a derivative of FK888), or a pro-drug or an active metabolite thereof, or a pharmaceutically acceptable salt thereof.

More preferably, said second compound is MK-0869 and is administered in a dose ranging between 10 and 160 mg of the active ingredient, even more preferred is a dose of 80 mg of the active ingredient.

The invention also relates to a method for treating a disease or disorder with an underlying dysregulation of the emotional functionality, for instance a method for treating a disease or disorder with an underlying dysregulation of the emotional functionality, for instance, selected from the group comprising mood disorders, anxiety disorders, schizophrenia and other psychotic disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect; comprising the use of a composition comprising a first compound having (i) a selective affinity for the D4 receptor with a pKi value equal to or higher than 8 towards the D4 receptor and less than 8 towards other Dopamine receptors, and a second compound having (ii) a selective affinity for the 5-HT2A receptor with a pKi value equal to or higher than 8 towards the 5-HT2A receptor and less than 8 towards other 5HT receptors.

In a preferred embodiment of the invention, said first compound is chosen from the group comprising PIPAMPERONE, FANANSERIN, L-745,870, PNU-101387G and U-101387 and wherein said second compound is chosen from the group comprising PIPAMPERONE, FANANSERIN, ORG 5222, ZOTEPINE, OLANZEPINE, CLOZAPINE, S16924, S18327, AMPEROZIDE, SERTINDOLE, MDL 100.907, TIOSPIRONE, FLUSPIRILENE, OCAPERIDONE, RISPERIDONE and ZIPRASIDONE or a pro-drug or an active metabolite thereof, or a pharmaceutically acceptable salt thereof.

In a more preferred embodiment said composition is administered to a patient in a dose ranging between 0.5 μg and 300 mg for each of the active ingredients.

According to separate embodiments of the invention, for the following compounds, the following doses (daily doses) are preferred: PIPAMPERONE: 5 to 15 mg; ORG 5222: 1-10 mg; OLANZEPINE: 1-10 mg; CLOZAPINE: 1-200 mg; SERTINDOLE: 0.5-4 mg; OCAPERIDONE: 0.5-2 MICROGRAM; RISPERIDONE: 0.5-2 MG and ZIPRASIDONE: 1-20 MG.

According to yet another embodiment, the invention relates to a composition as defined above for treating a disease or disorder with an underlying dysregulation of the emotional functionality, for instance, selected from the group comprising mood disorders, anxiety disorders, schizophrenia and other psychotic disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect; wherein said composition is administered simultaneously with, separate from or sequential to a third compound to augment the therapeutic effect of said third compound on said disease or to provide a faster onset of the therapeutic effect of said third compound on said disease.

According to a preferred embodiment, said third compound is a selective serotonin re-uptake inhibitor. In a preferred embodiment, the first and second compound are administered daily at least one day before administering said third compound. Preferably said third compound is a selective serotonin re-uptake inhibitor chosen from the group comprising CITALOPRAM, fluoxetine, venlafaxine, fluvoxamine, paroxetine, sertraline, milnacipran and duloxetine or a pro-drug or an active metabolite thereof, or a pharmaceutically acceptable salt thereof. More preferably said serotonin re-uptake inhibitor is CITALOPRAM and is administered in a dose ranging between 10 and 40 mg of the active ingredient.

According to another preferred embodiment, said third compound is a nor-epinephrine re-uptake inhibitor, preferably chosen from the group comprising, but not limited to, tandamine, pirandamine, ciclazindol, fluparoxan, lortalamine, talsupram, talopram, prindamine, nomifensine, viloxazine, tomoxetine, duloxetine, venlafaxine, milnacipran and reboxetine, or a pro-drug or an active metabolite thereof, or a pharmaceutically acceptable salt thereof.

According to another preferred embodiment, said third compound is a neuroleptic agent, preferably chosen from the group comprising, but not limited to, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, DU-127090, ORG-5222, SM-13496, amisulpride, CP-361428, Lu 35-138, balaperidone, S-18327, WAY-135452, eplivanserin, E-5842, SR-31742, NE-100, osanetant, SR-141716, SR-48692, BSF-201640, BSF-190555, LAX-101a, sarizotan, CX-691 and SB-271046, or a pro-drug or active metabolite thereof, or a pharmaceutically acceptable salt thereof.

According to another preferred embodiment, said third compound is an NK1 antagonist, preferably chosen from the group comprising but not limited to MK-0869, GW597599, GW679769, GW823296, Compound A, NKP608, CP-96,345 (cis-3-(2-methoxybenzyl-amino-2-benzhydrylquinuclidine), CP-122721, CP-99994, GR-82334 (D-Pro9-[Spiro-y-lactam]-Leu10,Trp11)-Physalaemin(1-11)), R673, TAK-637, RPR100893 (perhydroisoindolol), RP-67580, LY303870, SR-140333 and trans-4-hydroxy-1-(1H-indol-3-ylcarbonyl)-L-prolyl-N-methyl-N-(phenylmethyl)-L-tyrosineamide (a derivative of FK888), or a pro-drug or an active metabolite thereof, or a pharmaceutically acceptable salt thereof.

More preferably, said third compound is MK-0869 and is administered in a dose ranging between 10 and 160 mg of the active ingredient; even more preferred in a dose of 80 mg of the active ingredient.

In a further embodiment, the invention also relates to a method for treating a muscoskeletal disease or disorder comprising the use of a compound having (i) a selective affinity for the Dopamine-4 (D4) receptor with a pKi value equal to or higher than 8 towards the D4 receptor and less than 8 towards other Dopamine receptors, and (ii) a selective affinity for the 5-HT2A receptor with a pKi value equal to or higher than 8 towards the 5-HT2A receptor and less than 8 towards other 5HT receptors, or a composition comprising a first compound having a selective affinity for the D4 receptor with a pKi value equal to or higher than 8 towards the D4 receptor and less than 8 towards other Dopamine receptors, and a second compound having a selective affinity for the 5-HT2A receptor with a pKi value equal to or higher than 8 towards the 5-HT2A receptor and less than 8 towards other 5HT receptor, characterized in that said compound or composition is administered simultaneously with, separate from or sequential to a COX-2 inhibitor to augment the therapeutic effect of said COX-2 inhibitor or to provide a faster onset of the therapeutic effect of said COX-2 inhibitor.

According to a preferred embodiment, the musculoskeletal disease or disorder is selected from the group comprising, but not limited to, rheumatoid arthritis, osteoarthritis or ankylosing spondylitis.

In a further preferred embodiment, the COX-2 inhibitor is chosen from the group comprising, but not limited to, celecoxib, rofecoxib, meloxicam, piroxicam, deracoxib, parecoxib, valdecoxib, etoricoxib, a chromene derivative, a chroman derivative, N-(2-cyclohexyloxynitrophenyl)-methane sulfonamide, COX189, ABT963 and JTE-522, or a pro-drug or active metabolite thereof, or a pharmaceutically acceptable salt thereof.

The invention also relates to a method for preparing a compound having a selective D4 and 5-HT2A antagonist, reverse agonist or partial agonist activity comprising the following steps: (a) measuring the selective affinity of a test compound to the D4 receptor and selecting a compound that has a pKi value equal to or greater than 8 towards the D4 receptor in respect to all the other D receptors, and measuring the selective efficacy of the selected compound to the D4 receptor and selecting a compound which is a selective antagonist, inverse agonist or partial agonist of the D4 receptor; (b) measuring the selective affinity of a test compound to the 5-HT2A receptor and selecting a compound that has a pKi value equal to or greater than 8 towards the 5-HT2A receptor in respect to all the other 5HT receptors, and measuring the selective efficacy of the selected compound to the 5-HT2A receptor and selecting a compound which is a selective antagonist, inverse agonist or partial agonist of the 5-HT2A receptor; (c) identifying a compound which is selected in (a) and (b), (d) preparing the compound identified in (c).

The invention further also relates to a compound prepared by the described method.

DETAILED DESCRIPTION OF THE INVENTION

The present inventor has surprisingly found that compounds which have a high selective affinity towards the 5-HT2A receptor and which, at the same time have a high selective affinity towards the Dopamine-4 (D4) receptor show an improved effect in treating underlying dysregulation of the emotional functionality of mental disorders.

The compounds according to the invention may be chemical or biological in nature, or may be chemically synthesised. Preferably, the compounds of the invention are provided as a pharmaceutically acceptable salt.

One example of such a compound which has both a selective affinity for the 5-HT2A receptor with a pKi value equal to or higher than 8 towards the 5-HT2A receptor and less than 8 towards other 5HT receptors, and a selective affinity for the D4 receptor with a pKi value equal to or higher than 8 towards the D4 receptor and less than 8 towards other Dopamine receptors is PIPAMPERONE. PIPAMPERONE is the conventional name given for the compound of the formula 1'-[3-(p-Fluorobenzoyl)propyl]-[1,4'-bipiperidine]-4'-carboxamide. PIPAMPERONE is also the active ingredient of Dipiperon (Janssen, Cilag B. V).

Further, the present inventor has surprisingly found that the dosage of active ingredient for PIPAMPERONE in treatment could be very low compared to conventionally used dosages. Preferred dosages which, according to the invention, have been shown to be effective for treating these mental disorders, range between 5 and 15 mg per day or between 5 and 10 mg per day. More preferably, dosages of 5, 6, 7, 8, 9, 10, 11, 12, 13, 14 or 15 mg per day are used in treatment of the diseases of the invention. In conventional PIPAMPERONE treatment, the active ingredient is available in tablets of 40 mg per tablet or in solutions of 2 mg per drop. Conventional usage of high doses ranging from 40 to 360 mg is prescribed. For instance for children up to the age of 14, a doses corresponding with 2 to 6 mg per kg body weight is conventionally prescribed. The high selective affinity of PIPAMPERONE towards the 5-HT2A receptor and the D4 receptor is reflected in the low dosage which is needed for the treatment of the mental diseases listed below and also contributes to the efficacy of the treatment.

The mental disorders which can be treated using PIPAMPERONE in a mono therapy at such low doses are for instance anxiety disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

Mental disorders such as depression are commonly treated with serotonin re-uptake inhibitors. Unfortunately, however, these compounds can give rise to side effects in use. Moreover, a substantial problem in most treatment of mental disorders is the non-response to selective serotonin re-uptake inhibitors (SSRIs). Also the onset of the therapeutic effect can be delayed undesirable.

A problem to be solved by the present invention is thus the provision of a more efficient therapy and efficient, highly selective and efficacious medicaments for treating mental disorders.

The inventor has found that the non-response to selective serotonin re-uptake inhibitors (SSRIs) in depression may be declared by (partial) inhibition of the 5-HT1A stimulation via 5-HT2A stimulation. Des-inhibition thereof via 5-HT2A antagonism seems to be an answer to this problem.

The present inventor has found that a simultaneous or foregoing treatment with a compound having a high selective 5-HT2A antagonist, inverse agonist or partial agonist activity, could lead to a greater response towards SSRIs. However, not all compounds exhibiting 5-HT2A antagonism are useful: competition between 5-HT2A stimulation via serotonin and 5-HT2A antagonism via the compound could be responsible for the lack of more efficacy of compounds which have both a selective serotonin re-uptake inhibitory and 5-HT2A antagonist profile, such as trazodone and nefazodone.

The present inventor has further surprisingly found that a simultaneous or foregoing treatment with a compound having a high selective D4 antagonist, inverse agonist or partial agonist activity in combination with a compound having a high selective 5-HT2A antagonist, inverse agonist or partial agonist activity could lead to a greater response towards SSRIs.

The present inventor has found that a compound which binds to the 5-HT2A receptor with a pKi of at least 8 but for which the binding affinity, ie pKi, towards other 5HT receptors is less than 8 in combination with a compound which has a high selective affinity for the D4 receptor, i.e. which bind to the D4 receptor with a pKi of at least 8 but for which the binding affinity, ie pKi, towards other dopamine receptors is less than 8 also show such an improved effect in treatment. These effects, ie D4 antagonism, inverse agonism or partial agonism and 5-HT2A antagonism, inverse agonism or partial agonism, preferably reside in the same compound. In other embodiments of the invention, these effects reside in separate compounds.

'Other 5HT receptors' as used herein are for instance 5-HT1 receptors (i.e. 5-HT1A, 5-HT1B, 5-HT1D, 5-HT1E, 5-HT1F), 5-HT2B, 5-HT2C, 5-HT6 (rat) and 5-HT7 (rat).

5-HT2A responsive compounds according to the invention are, for instance PIPAMPERONE, FANANSERIN, L-745, 870, PNU-101387G and U-101387. All these compounds are known in the art and are to be used in doses according to the supplier's or physician's prescription.

By the expression 'selective affinity for the 5-HT2A receptor' is meant that the receptor has a higher affinity for the 5-HT2A receptor than for other 5-HT receptors.

Preferably, the compounds of the invention which have a selective affinity for the 5-HT2A receptor, are compounds which have a pKi value equal to or higher than 8 towards the 5-HT2A receptor and less than 8 towards other 5HT receptors, as can be measured, for instance by methods known in the art. For instance, the "NIMH Psychoactive Drug Screening Program (PDSP)" $K_i$ database http://kidb.cwru.edu/nimh/5htp.php), is a unique resource in the public domain which provides information on the abilities of drugs to interact with an expanding number of molecular targets. The PDSP $K_i$ database serves as a data warehouse for published and internally-derived pKi, or affinity, values for a large number of drugs and drug candidates at an expanding number of G-protein coupled receptors, ion channels, transporters and enzymes. The PDSP internet site also provides for commonly used protocols and assays for measuring pKi values of 5HT receptors.

The expression 'selective affinity for the D4 receptor' means that the receptor has a higher affinity for the Dopamine D4 receptor than for other Dopamine receptors.

D4 responsive compounds according to the invention are, for instance, PIPAMPERONE, FANANSERIN, ORG 5222, ZOTEPINE, OLANZEPINE, CLOZAPINE, S16924, S18327, AMPEROZIDE, SERTINDOLE, MDL 100.907, TIOSPIRONE, FLUSPIRILENE, OCAPERIDONE, RISPERIDONE and ZIPRASIDONE. All these compounds are known in the art and are to be used in doses according to the supplier's or physician's prescription.

'Other Dopamine receptors' are, for instance, D1, D2 and D3.

pKi values of test compounds for Dopamine receptors can be measured using commonly known assays.

Compounds which have a selective affinity for the D4 receptor preferably have a pKi value equal to or higher than 8 towards the D4 receptor and less than 8 towards other Dopamine receptors.

A preferred example of a compound which has both a selective affinity for the 5-HT2A receptor with a pKi value equal to or higher than 8 towards the 5-HT2A receptor and less than 8 towards other 5HT receptors, and a selective affinity for the D4 receptor with a pKi value equal to or higher than 8 towards the D4 receptor and less than 8 towards other Dopamine receptors and which is therefore useful in a combination therapy is PIPAMPERONE.

Table 1 illustrates the selective affinity of for instance PIPAMPERONE for the 5-HT2A and for the D4 receptor. In addition, Table 1 also illustrates the low or absence of affinity of PIPAMPERONE for other receptors such as the adrenergic receptors Alpha 1A, Alpha 2A, Alpha 2B, Alpha 2C, Beta1, Beta2, and the histamine receptor H1. As such, treating patients with PIPAMPERONE will provide for less side effects which otherwise result from simultaneous stimulation of other receptors. Therefore, and according to preferred embodiments, useful compounds according to the invention not only have a selective 5-HT2A and/or D4 affinity but also a low affinity for other receptors such as the adrenergic and histamine receptors.

The low dosage which can be used in PIPAMPERONE treatment, as already described earlier, contributes to the high selective affinity of the compound towards the 5-HT2A receptor and the D4 receptor and therefore also to the efficacy of the treatment.

The mental disorders which can be treated using compounds having a high selective affinity for the 5-HT2A and D4 receptor, for instance PIPAMPERONE, in a combination therapy with an SSRI are for instance mood disorders, anxiety disorders, schizophrenia and other psychotic disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

These diseases and their diagnosis are very clearly defined in the "Diagnostic and Statistical Manual of Mental Disorders" published by the American Psychiatric Association. This manual sets forth diagnostic criteria, descriptions and other information to guide the classification and diagnosis of mental disorders and is commonly used in the field of neuropsychiatry. It is for instance available on the internet under: http://www.behavenet.com/capsules/disorders/dsm4tr.htm.

According to a preferred embodiment, the invention thus relates to the use of a compound having a high selective affinity for the 5-HT2A and D4 receptor in combination with a selective serotonin re-uptake inhibiter, for instance chosen from the group comprising CITALOPRAM, fluoxetine, venlafaxine, fluvoxamine, paroxetine, sertraline, milnacipran and duloxetine or a pro-drug or an active metabolite thereof, or a pharmaceutically acceptable salt thereof.

The terms "treatment", "treating", and the like, as used herein include amelioration or elimination of a developed mental disease or condition once it has been established or alleviation of the characteristic symptoms of such disease or condition. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. It should be clear that mental conditions may be responsible for physical complaints. In this respect, the term "treating" also includes prevention of a physical disease or condition or amelioration or elimination of the developed physical disease or condition once it has been established or alleviation of the characteristic symptoms of such conditions.

As used herein, the term "medicament" also encompasses the terms "drug", "therapeutic", "potion" or other terms which are used in the field of medicine to indicate a preparation with therapeutic or prophylactic effect.

The present inventor has not only found that the selective 5-HT2A and D4 antagonists, inverse agonists or partial agonists have an effect in augmenting the therapeutic effect or in providing a faster onset of the therapeutic effect of selective serotonin re-uptake inhibitors, but also that this effect is seen in therapy with other pharmaceutical compounds. A few examples of other pharmaceutical compounds whose effects are augmented or where the onset of the effect is fastened upon simultaneous or fore-going treatment with a 5-HT2A and D4 antagonist, inverse agonist or partial agonist, are nor-epinephrine re-uptake inhibitors, neuroleptic agents, NK1 antagonists or compounds used for treating or alleviating musculoskeletal diseases or disorders. It should be clear, given the general applicable character of the invention, that this list of other pharmaceutical compounds is very brief and that the invention should not be restricted to the ones exemplified herein.

According to the invention it thus has been found that the compounds having a selective 5-HT2A and D4 antagonist, inverse agonist or partial agonist activity as described above are useful for augmenting the therapeutic effect of a second compound on a disease.

According to another embodiment of the invention it has also been found that the compounds having a selective 5-HT2A and D4 antagonist, inverse agonist or partial agonist activity as described above are useful for providing a faster onset of the therapeutic effect of a second compound on a disease.

In one embodiment, the compound having a selective 5-HT2A and D4 antagonist, inverse agonist or partial agonist activity is used in a combination therapy with the second compound are to treat the same disease or disorder, for instance a disease selected from the group comprising mood disorders, anxiety disorders, schizophrenia and other psychotic disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

Preferably, said second compound is a nor-epinephrine re-uptake inhibitor. Preferred nor-epinephrine re-uptake inhibitors to be administered in combination with the selective 5-HT2A and D4 antagonist, inverse agonist or partial agonist of the invention are chosen from the group comprising tandamine, pirandamine, ciclazindol, fluparoxan, lortalamine, talsupram, talopram, prindamine, nomifensine, viloxazine, tomoxetine, duloxetine, venlafaxine, milnacipran and reboxetine, pharmaceutically acceptable salts, pro-drugs and mixtures thereof. In other preferred embodiments, said second compound is a neuroleptic agent. Preferred neuroleptic agents to be administered in combination with the selective 5-HT2A and D4 antagonist, inverse agonist or partial agonist of the invention are chosen from the group comprising chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, DU-127090, ORG-5222, SM-13496, amisulpride, CP-361428, Lu 35-138, balaperidone, S-18327, WAY-135452, eplivanserin, E-5842, SR-31742, NE-100, osanetant, SR-141716, SR-48692, BSF-201640, BSF-190555, LAX-101a, sarizotan, CX-691 and SB-271046, pharmaceutically acceptable salts, pro-drugs or active metabolites thereof, or mixtures thereof. In other preferred embodiments, said second compound is an NK1 antagonist. Preferred NK1 antagonists to be administered in combination with the selective 5-HT2A and D4 antagonist, inverse agonist or partial agonist of the invention are chosen from the group comprising MK-0869, GW597599, GW679769, GW823296, Compound A, NKP608, CP-96,345 (cis-3-(2-methoxybenzyl-amino-2-benzhydrylquinuclidine), CP-122721, CP-99994, GR-82334 (D-Pro9-[Spiro-y-lactam]-Leu10,Trp11)-Physalaemin(1-11)), R673, TAK-637, RPR100893 (perhydroisoindolol), RP-67580, LY303870, SR-140333 and trans-4-hydroxy-1-(1H-indol-3-ylcarbonyl)-L-prolyl-N-methyl-N-(phenylmethyl)-L-tyrosineamide (a derivative of FK888), pharmaceutically acceptable salts, pro-drugs or active metabolites thereof, or mixtures thereof.

It should be noted that these compounds might be known under other names. For instance 'aprepitant' is the generic name for MK-0869 whereas it is known as EMEND as its trademark name (Merck, Whitehouse Station, N.J.).

In alternative embodiments, the second compound is used to treat another disease. In a preferred embodiment, said second compound is a COX-2 inhibitor and is used for treating musculoskeletal diseases or for the management of acute pain or for primary treatment of dysmenorrhea, and the first compound augments the therapeutic effect or provides for a faster onset of the therapeutic effect of said second compound on said other disease.

Preferred COX-2 inhibitors to be administered in combination with the selective 5-HT2A and D4 antagonist, inverse agonist or partial agonist of the invention are chosen from the group comprising celecoxib, rofecoxib, meloxicam, piroxicam, deracoxib, parecoxib, valdecoxib, etoricoxib, a chromene derivative, a chroman derivative, N-(2-cyclohexyloxynitrophenyl)-methane sulfonamide, COX189, ABT963 or JTE-522, pharmaceutically acceptable salts, pro-drugs or active metabolites thereof, or mixtures thereof.

From the above it should be clear that the selective 5-HT2A and D4 antagonist, inverse agonist or partial agonist is also named 'the first compound' in the embodiments of the invention.

According to the invention, when the 5-HT2A and D4 antagonist, inverse agonist or partial agonist activity reside in separate compounds, the term "composition" will be used. Compositions of the invention comprise a first compound having (i) a selective affinity for the D4 receptor with a pKi value equal to or higher than 8 towards the D4 receptor and less than 8 towards other Dopamine receptors, and a second compound having (ii) a selective affinity for the 5-HT2A receptor with a pKi value equal to or higher than 8 towards the 5-HT2A receptor and less than 8 towards other 5HT receptors.

The expression "the 5-HT2A and D4 antagonist, inverse agonist or partial agonist" is used herein to indicate a single compound having both activities or to indicate the composition comprising the activity in separate compounds.

It should be clear that when, in the present invention, a composition of separate compounds is used instead of a single compound, they may be used in combination with another, i.e. a third, compound to augment the therapeutic effect of the other, i.e. the third, compound on the same or another disease.

When the 5-HT2A and D4 antagonist, inverse agonist or partial agonist and the second compound or third compound, are administered simultaneously, the compounds or active ingredients may be present in a single pharmaceutical composition or formulation. Alternatively the compounds or active ingredients are administered in separate pharmaceutical compositions or formulations for simultaneous or separate use.

When the 5-HT2A and D4 antagonist, inverse agonist or partial agonist of the invention is administered prior to the second or third compound, as defined, the 5-HT2A and D4 antagonist, inverse agonist or partial agonist is administered at least during 1 day prior to said second or third compound. Preferably the 5-HT2A and D4 antagonist, inverse agonist or partial agonist is administered for at least 1, 2, 3, 4, 5, 6, 7, 8, 9 or 10 days, prior to the administration of the second or third compound. Preferably the 5-HT2A and D4 antagonist, inverse agonist or partial agonist is administered for at least 2, 3, 4, 5 weeks prior to the administration of the second or third compound, or for at least 1, 2, 3, 4, 5, 6, 7, 8, 9, 10, 11 or 12 months prior to the administration of the second or third compound.

According to a preferred embodiment of the invention, the above described compounds having a 5-HT2A and D4 antagonist, inverse agonist or partial agonist activity are useful for augmenting the therapeutic effect of CITALOPRAM or for providing a faster onset of the therapeutic effect of CITALOPRAM.

CITALOPRAM or citalopram hydrobromide is a selective serotonin (5-hydroxytryptamine/5-HT) re-uptake inhibitor (SSRI) and is the conventional name given for the compound of the formula (RS)-1-[3-(dimethylamino)propyl]-1-(p-flurophenyl)-5-phthalancarbonitrile, hydro-bromide.

According to one embodiment, a daily doses of active ingredient of SSRI, preferably CITALOPRAM, ranges between 10 and 40 mg per day. Preferably, daily doses of active ingredient ranging between 20 and 30 mg per day are administered. More preferably, a daily dose of 10, 15, 20, 25, 30, 35 or 40 mg per day is administered.

Other preferred second or third compounds according to the invention are chosen from the group comprising selective serotonin re-uptake inhibitors, for instance CITALOPRAM, fluoxetine, venlafaxine, fluvoxamine, paroxetine, sertraline, milnacipran and duloxetine; COX-2 inhibitors, for instance celecoxib, rofecoxib, meloxicam, piroxicam, deracoxib, parecoxib, valdecoxib, etoricoxib, a chromene derivative, a chroman derivative, N-(2-cyclohexyloxynitrophenyl) methane sulfonamide, COX189, ABT963 or JTE-522; nor-epinephrine re-uptake inhibitors, for instance tandamine, pirandamine, ciclazindol, fluparoxan, lortalamine, talsupram, talopram, prindamine, nomifensine, viloxazine, tomoxetine, duloxetine, venlafaxine, milnacipran and reboxetine; and neuroleptic agents, for instance chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, DU-127090, ORG-5222, SM-13496, amisulpride, CP-361428, Lu 35-138, balaperidone, S-18327, WAY-135452, eplivanserin, E-5842, SR-31742, NE-100, osanetant, SR-141716, SR-48692, BSF-201640, BSF-190555, LAX-101a, sarizotan, CX-691 and SB-271046; and NK1 antagonists, for instance MK-0869, GW597599, GW679769, GW823296, Compound A, NKP608, CP-96,345 (cis-3-(2-methoxybenzyl-amino-2-benzhydrylquinuclidine), CP-122721, CP-99994, GR-82334 (D-Pro9-[Spiro-y-lactam]-Leu10,Trp11)-Physalaemin(1-11)), R673, TAK-637, RPR100893 (perhydroisoindolol), RP-67580, LY303870, SR-140333 and trans-4-hydroxy-1-(1H-indol-3-ylcarbonyl)-L-prolyl-N-methyl-N-(phenylmethyl)-L-tyrosineamide (a derivative of FK888). All these compounds are known in the art and are to be used in doses according to the supplier's or physician's prescription. Preferably, MK-0869 is used in doses ranging from 10 to 160 mg, more preferably a dose of 80 mg is administered.

Also encompassed by the invention are pro-drugs to these second or third compounds or active metabolites of these compounds. For instance, for risperidone it is known that, among other products, biotransformation in the liver produces 9-hydroxyrisperidone, which is of the same pharmacological activity and intensity as parent risperidone. Therefore, also 9-hydroxyrisperidone, naturally produced or chemically synthesized may be used in the methods of the invention.

The term "active metabolite" as used herein relates to a therapeutically active compound produced by the metabolism of a parent drug. Drugs administered to treat diseases are usually transformed (metabolized) within the body into a variety of related chemical forms (metabolites), some of which may have therapeutic activity (an active metabolite).

According to a yet more specific embodiment, the invention relates to a method for treating a disease or disorder with an underlying dysregulation of the emotional functionality comprising the use of PIPAMPERONE, further characterised in that PIPAMPERONE is administered simultaneously with, separate from or sequential to an NK1 antagonist to augment the therapeutic effect of said NK1 antagonist, or to provide a faster onset of the therapeutic effect of said NK1 antagonist; preferably said NK1 antagonist is chosen from the group comprising MK-0869, GW597599, GW679769, GW823296, Compound A, NKP608, CP-96,345 (cis-3-(2-methoxybenzyl-amino-2-benzhydrylquinuclidine), CP-122721, CP-99994, GR-82334 (D-Pro9-[Spiro-y-lactam]-Leu10,Trp11)-Physalaemin(1-11)), R673, TAK-637, RPR100893 (perhydroisoindolol), RP-67580, LY303870, SR-140333 and trans-4-hydroxy-1-(1H-indol-3-ylcarbonyl)-L-prolyl-N-methyl-N-(phenylmethyl)-L-tyrosineamide (a derivative of FK888), or a pro-drug or an active metabolite thereof, or a pharmaceutically acceptable salt thereof; more preferably said NK1 antagonist is MK-0869 and is administered in a dose ranging between 10 and 160 mg of the active ingredient; even more preferably said NK1 antagonist is administered in a dose of 80 mg of the active ingredient. In an even most preferred embodiment PIPAMPERONE, which is administered simultaneously with, separate from or prior to MK-0869, is administered in a dose ranging between 5 to 15 mg of the active ingredient.

The present invention also encompasses the use of these second or third compounds, administered in the form of a pharmaceutically acceptable salt in admixture with a suitable pharmaceutically acceptable excipient.

To prepare the pharmaceutical compositions, comprising the compounds or the combination of the first and second compound described herein, an effective amount of the active ingredients, in acid or base addition salt form or base form, is combined in admixture with a pharmaceutically acceptable carrier, which can take a wide variety of forms depending on the form of preparation desired for administration. These pharmaceutical compositions are desirably in unitary dosage form suitable, for administration orally, nasal, rectally, percutaneously or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included.

According to a further embodiment, the invention also relates to a method for preparing a compound having a selective D4 and 5-HT2A antagonist, reverse agonist or partial agonist. The invention also relates to the compounds prepared by the claimed method, with the proviso that said compound is not an already known compound, such as PIPAMPERONE.

It should be clear that the compounds and compositions described herein are useful for treating any patient in need thereof. As used herein the term "patient" is not restricted to humans but also to other mammals, for instance domestic animals which may also suffer from any form of a mental disease or disorder described herein.

The invention, now being generally described, will be more readily understood by reference to the following tables and examples, which are included merely for purposes of illustration of certain aspects and embodiments of the present invention and are not intended to limit the invention.

EXAMPLES

Example 1

Measuring pKi Values of Test Compounds

In Table 1, the pKi values of test compounds are given for each of the dopamine receptors, 5HT receptors, adrenergic receptors and the histamine1 receptor. The affinity of test compounds for the respective receptors has been performed according to conventional procedures known in the art.

An indication "0" means that no affinity has been measured between the test compound and the receptor.

The columns displaying the pKi values for the D4 and the 5-HT2A receptor are filled with dark grey. pKi values between 8 and 9 and higher than 9 are represented by light grey boxes.

Example 2

Foregoing Pipamperon-Citalopram Treatment in Mayor Depressive Disorder: a Placebo and Active Controlled Period Finding Clinical Trial Table 2 represents the set-up of a clinical trial comprising for treatment groups:

Group Plc—Active/Day 0 represents the group receiving 10 mg citalopram, twice a day, starting the first day (Day 0) of active treatment in the clinical trial. This administration regime is also indicated as the mono therapy.

Group Pip—Active/Day 0 represents the group receiving a combination of 4 mg pipamperon and 10 mg citalopram, twice a day, starting the first day (Day 0) of active treatment in the clinical trial. This administration regime is also indicated as the non-foregoing combo therapy.

Group Pip—Active/Day 4 represents the group receiving 4 mg pipamperon, twice a day, starting the first day (Day 0) of active treatment in the clinical trial, followed by a combination of 4 mg pipamperon and 10 mg citalopram, twice a day, starting the fifth (Day 4) day of active treatment in the clinical trial. This administration regime is also indicated as the foregoing therapy with combination therapy starting after 4 days of active treatment.

Group Pip—Active/Day 7 represents the group receiving 4 mg pipamperon, twice a day, starting the first day (Day 0) of active treatment in the clinical trial, followed by a combination of 4 mg pipamperon and 10 mg citalopram, twice a day, starting the eight (Day 7) day of active treatment in the clinical trial. This administration regime is also indicated as the foregoing therapy with combination therapy starting after 7 days of active treatment.

All subjects also undergo a placebo (PLC) run-in therapy, administered during a period of about 7 days before the active treatment starts.

During daily (D), weekly (W) or monthly (M) visits, several parameters are measured.

Under NECT is to be understood: Neuronal E-clinical Trial=Vesalius Expert development for this trial which includes the bottom-up measurement of:

In- and exclusion-criteria

Functional status evaluation

Medical history (Pre-)treatment signs & symptoms

DSM-IV rules for diagnosis & efficacy

HDRS-28 (Hamilton Depression Rating Scale—28 items)

Medical resource utilisation

Pre-trial & Concomittant medication

Drug administration (Serious) Adverse events

Admission to the acute and extension phase of treatment

Right flow of the trial

TABLE 1

| | D1 | D2 | D3 | D4 | $5HT_{1A}$ | $5HT_{1B}$ | $5HT_{1D}$ | $5HT_{1E}$ | $5HT_{1F}$ | $5HT_{2A}$ | $5HT_{2B}$ | $5HT_{2C}$ |
|---|---|---|---|---|---|---|---|---|---|---|---|---|
| ORG5222 | 8-9 | 8-9 | 8-9 | 8-9 | 8-9 | 8-9 | 8-9 | 7-8 | 0 | >9 | >9 | >9 |
| Zotepine | 0 | 8-9 | 8-9 | 7-8 | 6-7 | 7-8 | 7-8 | 6-7 | 0 | 8-9 | 0 | 0 |
| Fluparoxan | 0 | <6 | <6 | 0 | 6-7 | <6 | <6 | 0 | 0 | <6 | 0 | <6 |
| Olanzapine | 7-8 | 7-8 | 7-8 | 7-8 | <6 | 6-7 | 6-7 | <6 | 6-7 | 8-9 | 8-9 | 8-9 |
| Clozapine | 7-8 | 6-7 | 6-7 | 7-8 | 6-7 | 6-7 | 6-7 | 6-7 | 6-7 | 8-9 | 8-9 | 7-8 |
| S16924 | 0 | 7-8 | 7-8 | 7-8 | 8-9 | 0 | 0 | 0 | 0 | >9 | 8-9 | 7-8 |
| S18327 | 7-8 | 7-8 | 6-7 | 8-9 | 7-8 | 0 | 0 | 0 | 0 | 8-9 | 0 | 6-7 |
| Amperozide | 6-7 | 6-7 | 6-7 | <6 | <6 | 0 | 0 | 0 | 0 | 8-9 | 0 | <6 |
| GGR218231 | <6 | 7-8 | >9 | <6 | 6-7 | <6 | <6 | 0 | 0 | <6 | <6 | <6 |
| Sertindole | 7-8 | 8-9 | 8-9 | 7-8 | 6-7 | 7-8 | 7-8 | 6-7 | 6-7 | >9 | 0 | 8-9 |
| MDL100,907 | 6-7 | <6 | <6 | 6-7 | <6 | 0 | 0 | 0 | 0 | >9 | 0 | 7-8 |
| Haloperidol | 8-9 | >9 | 8-9 | 8-9 | <6 | 6-7 | <6 | <6 | <6 | 6-7 | <6 | <6 |
| Tiospirone | 7-8 | 8-9 | 8-9 | 8-9 | 8-9 | 0 | 0 | 0 | 0 | >9 | 0 | 8-9 |
| Raciopride | <6 | 8-9 | 8-9 | <6 | <6 | 0 | 0 | 0 | 0 | 6-7 | 0 | <6 |
| Fluspirilene | 0 | >9 | 8-9 | 8-9 | 7-8 | <6 | <6 | <6 | 0 | <6 | 0 | 0 |
| Ocaperidone | 7-8 | >9 | 8-9 | 8-9 | 7-8 | 0 | 0 | 0 | 0 | >9 | 0 | 7-8 |
| Risperidone | 7-8 | 8-9 | 7-8 | 8-9 | 6-7 | 8-9 | 6-7 | <6 | <6 | >9 | 0 | 7-8 |
| S33084 | 6-7 | 7-8 | >9 | <6 | <6 | 6-7 | 6-7 | 0 | 0 | 6-7 | 6-7 | 7-8 |
| L741626 | 6-7 | 8-9 | 7-8 | 6-7 | <6 | <6 | <6 | 0 | 0 | 6-7 | 6-7 | <6 |
| Seroquel | 6-7 | 6-7 | 6-7 | <6 | 6-7 | <6 | <6 | <6 | <6 | 6-7 | 6-7 | 6-7 |
| Yohimbine | 0 | 6-7 | <6 | 0 | 7-8 | 6-7 | 7-8 | 0 | 0 | <6 | 0 | <6 |
| Ziprasidone | 8-9 | 8-9 | 7-8 | 7-8 | 8-9 | >9 | 8-9 | 6-7 | 0 | >9 | 8-9 | 8-9 |
| Pipamperone | 0 | 6-7 | 6-7 | 8-9 | <6 | 6-7 | 6-7 | <6 | <6 | 8-9 | 0 | 0 |

| | $5HT_6$rat | $5HT_7$rat | Alpha1A | Alpha2A | Alpha2B | Alpha2C | Beta1 | Beta2 | H1 |
|---|---|---|---|---|---|---|---|---|---|
| ORG5222 | >9 | >9 | >9 | 8-9 | >9 | 7-8 | <6 | <6 | >9 |
| Zotepine | 0 | 0 | 0 | 6-7 | 8-9 | 6-7 | <6 | <6 | >9 |
| Fluparoxan | 0 | 0 | 6-7 | 8-9 | 8-9 | 8-9 | 0 | 0 | 0 |
| Olanzapine | 7-8 | 6-7 | 7-8 | 6-7 | 6-7 | 6-7 | <6 | <6 | >9 |
| Clozapine | 7-8 | 7-8 | 8-9 | 7-8 | 7-8 | 7-8 | <6 | <6 | >9 |
| S16924 | 7-8 | 7-8 | 8-9 | 6-7 | 7-8 | 6-7 | <6 | <6 | 0 |
| S18327 | 0 | 0 | >9 | 6-7 | 0 | 0 | 0 | 0 | 0 |
| Amperozide | 0 | 0 | 7-8 | <6 | 0 | 0 | 0 | 0 | 0 |
| GGR218231 | 0 | 0 | <6 | <6 | 0 | 0 | 0 | 0 | 0 |
| Sertindole | 0 | 0 | >9 | 6-7 | 6-7 | 6-7 | <6 | <6 | 6-7 |
| MDL100,907 | 0 | 0 | <6 | <6 | 0 | 0 | 0 | 0 | 0 |
| Haloperidol | <6 | 6-7 | 8-9 | <6 | 6-7 | <6 | <6 | <6 | 6-7 |
| Tiospirone | 0 | 0 | >9 | 6-7 | 0 | 0 | 0 | 0 | 0 |
| Raciopride | 0 | 0 | <6 | <6 | 0 | 0 | 0 | 0 | 0 |
| Fluspirilene | 0 | 0 | 0 | 6-7 | 7-8 | 7-8 | 6-7 | 6-7 | 7-8 |
| Ocaperidone | 0 | 0 | >9 | 0 | 0 | 0 | 0 | 0 | 0 |
| Risperidone | 0 | 0 | >9 | 7-8 | 8-9 | 8-9 | <6 | <6 | 7-8 |
| S33084 | 0 | 0 | 6-7 | <6 | 0 | 0 | 0 | 0 | 0 |
| L741626 | 0 | 0 | 6-7 | <6 | 0 | 0 | 0 | 0 | 0 |
| Seroquel | 0 | 6-7 | 7-8 | <6 | 7-8 | 6-7 | <6 | <6 | 8-9 |
| Yohimbine | 0 | 0 | 6-7 | 8-9 | 8-9 | >9 | <6 | <6 | 0 |
| Ziprasidone | 7-8 | 8-9 | 8-9 | 6-7 | 7-8 | 7-8 | <6 | <6 | 7-8 |
| Pipamperone | 0 | 0 | 0 | 6-7 | 7-8 | 6-7 | <6 | <6 | <6 |

TABLE 2

| VISITS Day/Week/ Month | ACUTE PHASE** V1 Screen minus D7 | V2 Base-line D0 | EXTENSION PHASE*** V3 D4 | V4 D7 | V5 W2 | V6 W3 | V7 W4 | V8 W6 | V9 W8 | V10 W10 | V11 W12 | V12 W16 | V13 W20 | V14 W24 | V15 M8 | V16 M10 | V17 M12 | FOLLOW-UP PHASE V18 W1 | V19 W2 |
|---|---|---|---|---|---|---|---|---|---|---|---|---|---|---|---|---|---|---|---|
| TREAT-MENT-GROUP | | | | | | | | | | | | | | | | | | | |
| Group Pip-Active/D7 | A | B | B | C | | | | | | | | | | | | | | A | A |
| Group Pip-Active/D4 | A | B | C | | | | | | | | | | | | | | | A | A |
| Group Pip-Active/D0 | A | C | | | | | | | | | | | | | | | | A | A |
| Group Pic-Active/D0 | A | D | | | | | | | | | | | | | | | | A | A |
| Informed Consent | x | | | | | | | | | | | | | | | | | | |
| NECT* | x | x | x | x | x | x | x | x | x | x | x | x | x | x | x | x | x | x | x |
| Vital Signs/ Weight | x | | | | | | | | | | | | | x | | | x | | x |
| LAB | x | | | | | | | | | | | | | x | | | x | | x |
| ECG | x | | | | | | | | | | | | | x | | | x | | x |
| Phys Exam | x | | | | | | | | | | | | | | | | | | |
| Alc/Drugs Screen | x | | | | | | | | | | | | | x | | | x | | x |
| CGI-S**** | x | x | x | x | x | x | x | x | x | x | x | x | x | x | x | x | x | x | x |
| Q-LES-Q***** | | | | | | | | | | | | | | | | | | | |

Treatment regimen:
A: PLC + PLC
B: 2 × (PLC + PIP(4 mg))/d
C: 2 × (CIT(10 mg) + PIP(4 mg))/d
D: 2 × (CIT(10 mg) + PLC)/d
*Neuronal E-Clinical Trial = Vesalius Expert Development for this Trial which includes the bottom-up measurement of:
**Entering Acute Phase: only NON-placebo responders as defined by the DSM-IV criteria of efficacy
***Entering Extension Phase: only remittors as defined by the DSM-IV criteria of efficacy
****CGI-S: Clinical Global Impressions-Improvement Scale
*****Q-LES-Q: Quality of Life, Enjoyment and Satisfaction Questionnaire

The invention claimed is:

1. A method for treating an anxiety disorder in a patient comprising administering to the patient a pharmaceutical composition comprising i) pipamperone in a dose of 5-15 mg and ii) citalopram in a dose of 10-40 mg.

2. The method of claim 1, wherein the pharmaceutical composition comprises pipamperone in a dose of 5 mg.

3. The method of claim 1, wherein the pharmaceutical composition comprises pipamperone in a dose of 10 mg.

4. The method of claim 1, wherein the pharmaceutical composition comprises pipamperone in a dose of 15 mg.

5. The method of claim 1, wherein the pharmaceutical composition comprises citalopram in a dose of 10 mg.

6. The method of claim 1, wherein the pharmaceutical composition comprises citalopram in a dose of 20 mg.

7. The method of claim 1, wherein the pharmaceutical composition comprises citalopram in a dose of 40 mg.

8. The method of claim 1, wherein the pharmaceutical composition comprises pipamperone in a dose of 15 mg and citalopram in a dose of 20 mg.

9. The method of claim 1, wherein the pharmaceutical composition is formulated for daily administration.

10. The method of claim 1, wherein the daily dose of pipamperone is 5-15 mg per day.

11. The method of claim 1, wherein the daily dose of pipamperone is 15 mg per day.

12. The method of claim 1, wherein the daily dose of citalopram is 10-40 mg per day.

13. The method of claim 1, wherein the daily dose of citalopram is 20 mg per day.

14. The method of claim 1, wherein the daily dose of pipamperone is 15 mg per day and the daily dose of citalopram is 20 mg per day.

15. The method of claim 1, wherein pipamperone is in the form of a pharmaceutically acceptable salt.

16. The method of claim 1, wherein citalopram is in the form of a pharmaceutically acceptable salt.

17. The method of claim 1, wherein the pharmaceutical composition is formulated for twice daily administration.

* * * * *